United States Patent
Schubert et al.

(10) Patent No.: US 8,383,045 B2
(45) Date of Patent: Feb. 26, 2013

(54) MEASURING UNIT FOR MEASURING CHARACTERISTICS OF A SAMPLE LIQUID, IN PARTICULAR VISCOELASTIC CHARACTERISTICS OF A BLOOD SAMPLE

(75) Inventors: Axel Schubert, Munich (DE); José Javier Romero-Galeano, Markt Schwaben (DE); Max Kessler, Munich (DE)

(73) Assignee: C A Casyso AG, Muttenz (CH)

( * ) Notice: Subject to any disclaimer, the term of this patent is extended or adjusted under 35 U.S.C. 154(b) by 204 days.

(21) Appl. No.: 12/688,306

(22) Filed: Jan. 15, 2010

(65) Prior Publication Data
US 2010/0184201 A1    Jul. 22, 2010

Related U.S. Application Data

(60) Provisional application No. 61/145,270, filed on Jan. 16, 2009.

(51) Int. Cl.
   G01N 33/00   (2006.01)
   G01N 33/86   (2006.01)
   G01N 11/14   (2006.01)
   G01N 37/00   (2006.01)

(52) U.S. Cl. .......... 422/73; 436/69; 73/54.28; 73/54.33; 73/54.35; 73/64.41

(58) Field of Classification Search ...... 73/54.33–54.35, 73/54.28, 64.41; 42/73
See application file for complete search history.

(56) References Cited

U.S. PATENT DOCUMENTS

| | | | |
|---|---|---|---|
| 3,714,815 A | 2/1973 | Hartert et al. | |
| 4,148,216 A | 4/1979 | Do et al. | |
| 4,193,293 A | 3/1980 | Cavallari | |
| 4,319,194 A | 3/1982 | Cardinal | |
| 4,765,180 A | * 8/1988 | Clifton | 73/54.33 |
| 5,287,732 A | 2/1994 | Sekiguchi | |
| 5,531,102 A | * 7/1996 | Brookfield et al. | 73/54.32 |

(Continued)

FOREIGN PATENT DOCUMENTS

| | | |
|---|---|---|
| DE | 27 40 932 A1 | 11/1978 |
| EP | 0404456 A2 | 12/1990 |

(Continued)

OTHER PUBLICATIONS

Rotem Brochure—"When Minutes Count to Stop the Bleeding," Pentapharm GmbH, www.rotem.de, Jun. 2007.

(Continued)

Primary Examiner — Jill Warden
Assistant Examiner — Charles D Hammond
(74) Attorney, Agent, or Firm — Jenkins, Wilson, Taylor & Hunt, P.A.

(57) ABSTRACT

The present invention is directed to a measuring unit, for measuring characteristics of a sample liquid, comprising a support member, having at least one upper bearing arm, with an upper bearing unit, at least one lower bearing arm, with a lower bearing unit, and a base, for being attachable to a respective measuring system; a shaft, having shaft toes and being rotatably supported about a rotation axis, by said upper bearing unit, and said lower bearing unit, wherein said upper bearing unit, said lower bearing unit, and said shaft toes form toe bearings, respectively; an interface member, having a detecting element, and a drive element, said interface member, being fixed on said shaft, and being connected to a coupling shaft, with a probe connector section, for measuring characteristics of said sample liquid; wherein said interface member, and the coupling shaft, are coaxially aligned with said shaft.

16 Claims, 7 Drawing Sheets

U.S. PATENT DOCUMENTS

| | | | |
|---|---|---|---|
| 5,777,212 A * | 7/1998 | Sekiguchi et al. | 73/54.33 |
| 5,777,215 A | 7/1998 | Calatzis et al. | |
| 5,902,937 A | 5/1999 | Amrani et al. | |
| 6,537,819 B2 | 3/2003 | Cohen | |
| 6,613,286 B2 | 9/2003 | Braun et al. | |
| 6,951,127 B1 * | 10/2005 | Bi | 73/54.37 |
| 7,399,637 B2 | 7/2008 | Wright et al. | |
| 8,110,392 B2 | 2/2012 | Battrell et al. | |
| 2002/0081741 A1 | 6/2002 | Braun, Sr. | |
| 2007/0059840 A1 | 3/2007 | Cohen et al. | |
| 2009/0130645 A1 | 5/2009 | Schubert et al. | |
| 2010/0154520 A1 | 6/2010 | Schubert et al. | |
| 2011/0237913 A1 | 9/2011 | Schubert et al. | |

FOREIGN PATENT DOCUMENTS

| | | |
|---|---|---|
| EP | 1627725 A2 | 2/2006 |
| EP | 1884778 | 2/2008 |
| GB | 2257256 A | 1/1993 |
| WO | WO 02/063273 A | 8/2002 |
| WO | WO2005/106467 | 11/2005 |
| WO | WO 2006/126290 | 11/2006 |
| WO | WO2008/093216 | 8/2008 |

OTHER PUBLICATIONS

European Search Report from EP 09150740 dated Jun. 30, 2009.
Hartert H: "Blood Coagulation Studies with Thromboelastography—A New Research Method," *Klin Wochenschrift*, 26:577-583, 1948—English translation.
European Search Report for EP 07121222 dated Apr. 9, 2008.
European Search Report for EP 08172769 dated Jun. 4, 2009.
Kawasaki et al., "The Effects of Vasoactive Agents, Platelet Agonists and Anticoagulation On Thrombelastography," *Acta Anaesthesiologica Scandinavica*, Oct. 2007, vol. 51, No. 9, pp. 1237-1244.
Rodzynek et al., "The Transfer Test: A New Screening Procedure for Thrombotic Diseases," *The Journal of Surgical Research*, Sep. 1983, vol. 35, No. 3, pp. 227-233.
Calatzis et al., "Strategies to Assess Individual Susceptibility to abciximab Therapy Using A New Functional Assay," *Annals of Hematology*, (Berlin, DE) vol. 76, No. Suppl 1, 1998, p. A61, XP009097526.
Salooja et al., "Thrombelastography," *Blood Coagulation & Fibrinolysis*, vol. 12, No. 5, 2001, pp. 327-337.
Rugeri et al., "Diagnosis of Early Coagulation Abnormalities in Trauma Patients by Rotation Thrombelastography," Journal of Thrombosis and Haemostasis, Feb. 2007, vol. 5, No. 2, pp. 289-295.
Chakroun et al., "The influence of Fibrin Polymerizatino and Platelet-Mediated Contractile Forces on Citrated Whole Blood Thromboelstography Profile," *Thrombosis and Haemostasis*, May 2006, vol. 95, No. 5, pp. 822-828.
Spannagl et al., "Point-of-Care Analysis of the Homostatic System," *Laboratoriumsmedizin*, (Kirchheim, DE), vol. 26, No. 1-2, Feb. 2002, pp. 68-76.
Shore-Lesserson et al., "Thromboelastography-guided transfusion algorithm reduces tranfusions in complex cardiac surgery," *Anesthesia and Analgesia*, Feb. 1999, vol. 88, No. 2, pp. 312-319.
Non-final Office Action for U.S. Appl. No. 12/275,757 dated Jan. 21, 2011.
International Search Report and Written Opinion for PCT/EP2010/050454 dated Apr. 20, 2010.
Office Action with Restriction/Election Requirement for U.S. Appl. No. 12/275,757 dated Sep. 15, 2010.
Interview Summary for U.S. Appl. No. 12/275,757 dated Dec. 12, 2011.
Noon et al., "Reduction of Blood Trauma in Roller Pumps for Long-term Perfusion" World J. Surg. (9), 1985, pp. 65-71.
Novotny et al., "Platelets Secrete a Coagulation Inhibitor . . . ", Blood 1988 (72), pp. 2020-2025.
Soria et al., "Fibrin Stabilizing Factor (F XIII) and Collagen Polymerization", Path. Biol. Suppl. 22 (86), 1974, pp. 1355-1357.
Srinivasa et al., "Thromboelastography: Where Is It and Where Is It Heading?" Int'l Anesthesiology Clinics, vol. 39, Iss. 1, Winter 2001, pp. 35-49.
Tanaka et al., "Thrombin Generation Assay and Viscoelastic Coagulation . . . " Anesthesia & Analgesia vol. 105, No. 4, Oct. 2007.
Non-Final Office Action for U.S. Appl. No. 12/275,757 dated Oct. 18, 2011.
Non-Final Office Action for U.S. Appl. No. 12/640,376 dated Aug. 15, 2012.

* cited by examiner

MEASURING UNIT FOR MEASURING CHARACTERISTICS OF A SAMPLE LIQUID, IN PARTICULAR VISCOELASTIC CHARACTERISTICS OF A BLOOD SAMPLE

CROSS-REFERENCE TO RELATED APPLICATIONS

This application claims the benefit of U.S. Provisional Application No. 61/145,270, filed Jan. 16, 2009, the entire disclosure of which is herein incorporated by reference.

FIELD OF THE INVENTION

The present invention relates to a measuring unit for measuring characteristics of a sample liquid, in particular viscoelastic characteristics of a blood sample. The present invention also relates to a corresponding measuring system.

It is essential for survival that a wound stops bleeding, i.e. that the body possesses an adequate mechanism for haemostasis. The process of blood clotting can be activated in the case of injuries or inflammations by either extrinsic or intrinsic factors, e.g. tissue factor (TF) or Hagemann factor (F XII), respectively.

The other main constituent of the final blood clot are the thrombocytes which are interconnected by the fibrin fibres and undergo a number of physiological changes during the process of coagulation.

Various methods have been introduced to assess the potential of blood to form an adequate clot and to determine the blood clots stability. Common laboratory tests such as thrombocyte counts or the determination of fibrin concentration provide information on whether the tested component is available in sufficient amount but lack in answering the question whether the tested component works properly under physiological conditions (e.g. the polymerisation activity of fibrinogen under physiological conditions can not be assessed by common optical methods). Besides that, most laboratory tests work on blood-plasma and therefore require an additional step for preparation and additional time which is unfavourable especially under POC (point of care) conditions.

Another group of tests which overcomes these problems is summarized by the term "viscoelastic methods". The common feature of these methods is that the blood clot firmness (or other parameters dependent thereon) is continuously determined, from the formation of the first fibrin fibres until the dissolution of the blood clot by fibrinolysis. Blood clot firmness is a functional parameter, which is important for haemostasis in vivo, as a clot must resist blood pressure and shear stress at the site of vascular injury. Clot firmness results from multiple interlinked processes: coagulation activation, thrombin formation, fibrin formation and polymerization, platelet activation and fibrin-platelet interaction and can be compromised by fibrinolysis. Thus, by the use of viscoelastic monitoring all these mechanisms of the coagulation system can be assessed.

A common feature of all these methods used for coagulation diagnosis is that the blood clot is placed in the space between a cylindrical pin and an axially symmetric cup and the ability of the blood clot to couple those two bodies is determined.

The first viscoelastometric method was called "thrombelastography" (Hartert H: Blutgerinnungsstudien mit der Thrombelastographie, einem neuen Untersuchungsverfahren. Klin Wochenschrift 26:577-583, 1948). In the thromboelastography, the sample as a sample liquid is placed in a cup that is periodically rotated to the left and to the right by about 5°, respectively. A probe pin is freely suspended by a torsion wire. When a clot is formed it starts to transfer the movement of the cup to the probe pin against the reverse momentum of the torsion wire. The movement of the probe pin as a measure for the clot firmness is continuously recorded and plotted against time. For historical reasons the firmness is measured in millimetres.

A common feature of all these methods used for coagulation diagnosis is that the blood clot is placed in the space between a cylindrical pin and an axially symmetric cup and the ability of the blood clot to couple those two bodies is determined.

Calatzis et al. (U.S. Pat. No. 5,777,215) describe a measuring illustrated in FIG. 1 which is known under the term thromboelastometry. Contrary to the modifications mentioned above, thromboelastometry is based on a cup 43 fixed in a cup holder 48 while a probe element 42 is actively rotated. For this purpose the probe element 42 is attached to a coupling shaft 35' which is suspended by a ball bearing 49 in a base plate 39 and has a drive element 32 connected to it. An oscillating motion perpendicular to the drawing plane induced at the opposite end of the drive element 32 is transformed into a periodically rotation of the coupling shaft 35' and the connected cup 43 around a rotation axis 20 by about 5° in each direction. As the sample liquid 44 begins to coagulate the motion amplitude of the coupling shaft 35' which is detected by e.g. the deflection of a light beam from detecting means 41 and a detecting element 31, e.g. a mirror, starts to decrease.

During coagulation the fibrin backbone creates a mechanical elastic linkage between the surfaces of the blood-containing cup 43 and the probe element 42 plunged therein. A proceeding coagulation process induced by adding one or more activating factor(s) can thus be observed. In this way, various deficiencies of a patient's haemostatic status can be revealed and can be interpreted for proper medical intervention.

A general advantage of viscoelastometric, e.g. thromboelastometric, techniques compared to other laboratory methods in this field therefore is that the coagulation process and the change of mechanical properties of the sample are monitored as a whole. This means that thromboelastometry does not only indicate if all components of the coagulation pathways are available in sufficient amounts but also if each component works properly.

Compared with the device mentioned above using a torsion wire thromboelastometry as shown in FIG. 1 has the advantage that a ball bearing provides a certain stability of the measuring device, e.g. the measuring device can be configured as a transportable device and used under POC (point of care) conditions.

SUMMARY OF THE INVENTION

It is a problem underlying the presented invention to provide an improved measuring unit for measuring characteristics of a sample liquid, in particular viscoelastic characteristics of a blood sample.

Directly connected to this invention is the problem to provide a corresponding improved measuring system for measuring viscoelastic characteristics of a sample liquid, in particular the coagulation characteristics of a blood sample liquid.

These problems are solved by the subject-matter of the independent claims. Preferred embodiments are set forth in the dependent claims.

In a first aspect, the present invention provides measuring unit for measuring characteristics of a sample liquid, in particular viscoelastic characteristics of a blood sample, comprising a support member having at least one upper bearing arm with an upper bearing unit, at least one lower bearing arm with a lower bearing unit and a base for being attachable to a respective measuring system; a shaft having shaft toes and being rotatably supported about a rotation axis by said upper bearing unit and said lower bearing unit, wherein said upper bearing unit, said lower bearing unit and said shaft toes form toe bearings, respectively; an interface member having a detecting element and a drive element, said interface member being fixed on said shaft and being connected to a coupling shaft with a probe connector section for measuring characteristics of said sample liquid; wherein said interface member and the coupling shaft are coaxially aligned with said shaft.

In a second aspect, the present invention provides a measuring system for measuring characteristics of a sample liquid, in particular viscoelastic characteristics of a blood sample, comprising at least one measuring unit according to the invention.

Toe bearings have clearances and friction losses which are decreased in relation to ball bearings. In particular it is advantageous that toe bearings have smaller clearances regarding tilting as well. The measuring device according to the invention also has the advantage to provide a unit which does not need a basement being aligned horizontally with high precision. Thus it is highly suitable for use in POC conditions and the like. Moreover the measuring unit according to the invention is more unsusceptible in case of vibrations than that one of the state of the art. Another advantage is the miniaturized shape of toe bearings.

The support member forms a structural rigid component of the measuring unit and supports the shaft by the toe bearings. The shaft is coupled to a coupling shaft by an interface member being a component with several functions.

Said upper bearing unit and said lower bearing unit are removable inserts each being fixed in said respective bearing arm of said support member. Thus it is possible to remove the bearing units together with the shaft in case of maintenance without changing the support member.

Said lower bearing unit is a thrust bearing and said upper bearing unit is a moveable bearing. The moveable bearing is configured to be adjustable by adjusting means to achieve optimal friction and clearances.

The bearing units are equipped with bearing plates made of e.g. kind of jewel, e.g. sapphire or/and ceramic.

The interface member comprises an upper connector section connected to said shaft. This forms a simple connection to the shaft.

Furthermore said interface member has a frame having an opening for a passage of said lower bearing arm of said support member, which allows for a compact assembly of the measuring unit and a connection to the coupling shaft.

Moreover a lower connector section for a connection to said coupling shaft forms another portion of the interface member.

Eventually the interface member has a front for securing that said detecting element thereon; and moreover a receptacle for securing that said drive element therein.

The interface member further comprises a fixing unit for fixing said interface member to said shaft. It is preferred that said fixing unit is at least one screw to achieve a simple fixing.

In an alternative embodiment said fixing unit is formed having clip means cooperating with corresponding clip means of said shaft.

It is preferred that said lower connector section is formed having clip means cooperating with corresponding clip means of an interface section of said coupling shaft for easy and fast connection without any tool.

It is also preferred that said probe connector section of said coupling shaft is formed having clip means cooperating with corresponding clip means of a probe element being detachably fixed onto said probe connector section. Thus an easy assembly and disassembly of different probe elements can be done.

In another preferred embodiment said detecting element can be a mirror.

When, in case of inserting the coupling shaft and/or a probe element onto the coupling shaft, an axial force can be exerted on the shaft and the interface member and cause an axial movement of the shaft in direction to the upper movable bearing. To limit said axial movement of the shaft and the interface member and a possible damage of the upper movable bearing the measuring unit can comprise axial stop means. Said stop means can be formed e.g. by a shoulder of the interface member or/and a shoulder of the shaft, said shoulder pointing to the upper bearing arm and co-operating with a corresponding shoulder of the upper bearing arm and/or the upper bearing unit.

In another embodiment at least one of said upper bearing unit and said lower bearing unit can comprises at least one bearing cover plate. Said bearing cover plate serves as a sealing and/or as a centre means for the shaft.

And in another embodiment it is preferred that the drive element is a spring wire.

Further features and advantages of the present invention will be evident from a description of embodiments with reference to the figures.

DESCRIPTION OF EXEMPLARY EMBODIMENTS

Parts and components having same functions are depicted with same references. Coordinate systems indicating x-, y- and z-direction in the figures allow for better orientation.

An exemplary embodiment of a measuring unit 1 according to the invention will now be described with regard to FIG. 2 and to FIG. 3.

Figure 2:
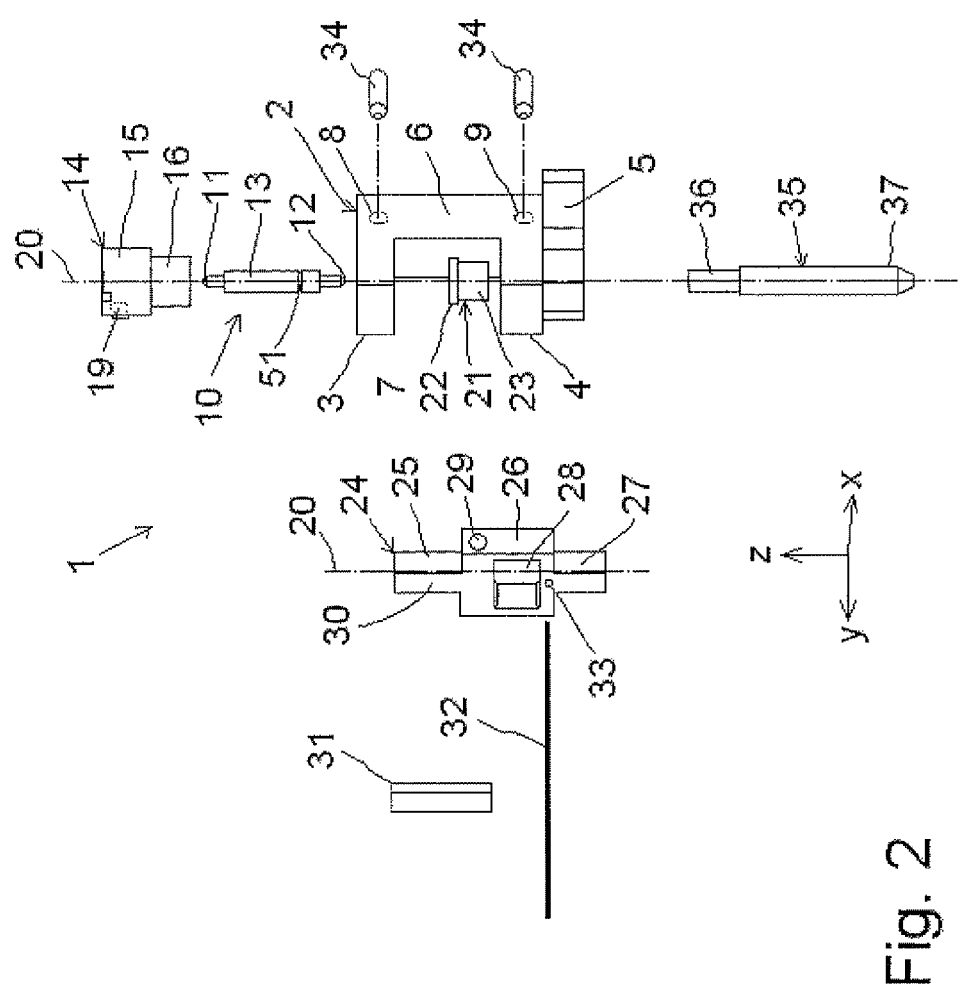
FIG. 2 is a perspective exploded view of an exemplary embodiment of a measuring unit according to the invention.
Figure 3:
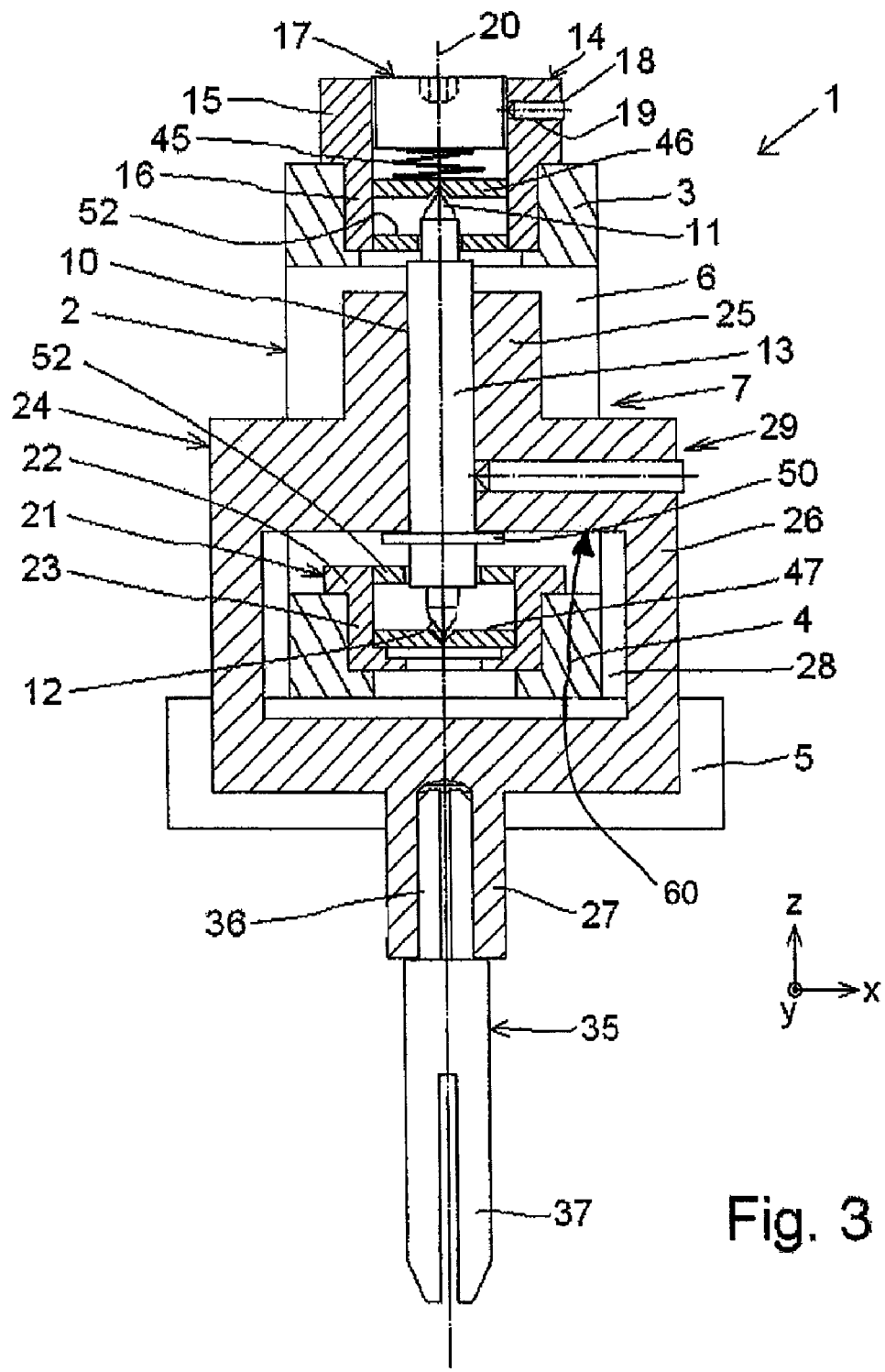
FIG. 3 is a schematic view along y-direction of a sectional view along a rotation axis 20 of the assembled measuring unit of FIG. 1

FIG. 2 is a perspective exploded view of an exemplary embodiment of the measuring unit 1 according to the invention and FIG. 3 is a schematic view along y-direction of a sectional view along a rotation axis 20 of the assembled measuring unit 1 of FIG. 2.

The measuring unit comprises a support member 2 with a body 6 extending in z-direction. The body 6 connects an upper bearing arm 3 and a lower bearing arm 4. The bearing arms 3 and 4 extending in x-direction are parallel to each other spaced with a distance. Body 6 and said bearing arms 3 and 4 form a U-shaped block having with a recess 7 with the distance defined by the bearing arms 3 and 4.

The body 6 and the lower bearing arm 4 are fixed onto a base 5 extending in x-direction. The base 5 comprises fixing holes (see FIG. 4 for mounting elements 38).

The upper bearing arm 3 is formed with a through hole for an upper bearing unit 14 and the lower bearing arm 4 has a through hole for a lower bearing unit 21, the through holes being aligned along a rotation axis 20.

The upper bearing unit 14 and the lower bearing unit 21 are formed as inserts to be inserted into said through holes. An upper fixing passage 8 extending from the side of the body 6 in the upper bearing arm 3 in y-direction allows for fixing the inserted upper bearing unit 14 by a fixing element 34, e.g. a screw. The inserted lower bearing unit 21 can be fixed similarly by a fixing element 34 via a lower fixing passage 9 extending in the lower bearing arm 4.

A shaft 10 with a shaft body 13 having an upper shaft toe 11 and a lower shaft toe 12 is provided to be supported by the bearing units 14 and 21. Said bearing units 14 and 21 are configured together with the shaft 10 having said upper shaft toe 11 and said lower shaft toe 12 to form a toe bearing, respectively. A groove 51 for a circlip 50 is formed in the shaft body 13.

The upper bearing unit 14 comprises a fixing section 15 and a bearing section 16. As can be seen from FIG. 3 the bearing section 16 is inserted into a through hole of the upper bearing arm 3. The upper bearing unit 14 is designed as a movable bearing with a movable bearing plate 46, e.g. made of a kind of jewel or ceramic, arranged in a through hole of the bearing unit 14. The upper shaft toe 11 of the shaft 10 rests on the movable bearing plate 46. The movable bearing plate 46 is movable along the rotation axis, i.e. in z-direction. A spring 45 is arranged in the fixing section 15 and can be adjusted by adjusting means 17, e.g. a screw, the adjusting means 17 being fixable by a fixing means 18, e.g. a screw through a fixing passage 19 in the fixing section 15.

The lower bearing unit 21 comprises a collar 22 and a bearing section 23. The bearing section 23 is inserted into a through hole of the lower bearing arm 4, wherein the collar 22 rests on the lower bearing arm 4. A thrust bearing plate 47 is arranged within a through hole of the lower bearing unit 21 and fixed therein. The trust bearing plate 47 is made of the material as the movable bearing plate, wherein the lower shaft toe 12 of the shaft 10 rests on the thrust bearing plate 47.

A pretension of the bearing units 14, 21 and the shaft 10 can be adjusted by the adjusting means 17.

The measuring unit 1 further comprises an interface member 24 having an upper connector section 25, a frame 26 and a lower connector section 27. An opening 28 is formed in the frame to form a passage having a cross-section greater than the cross-section of the lower bearing arm 4 (see also FIG. 3).

The upper connector section 25 is designed with a bore to be connected to the shaft 10 as can be seen from FIG. 3, wherein the shaft 10 is fixed by a fixing unit 29, e.g. a screw, to connect the interface member 24 to the shaft 10.

Figure 1:
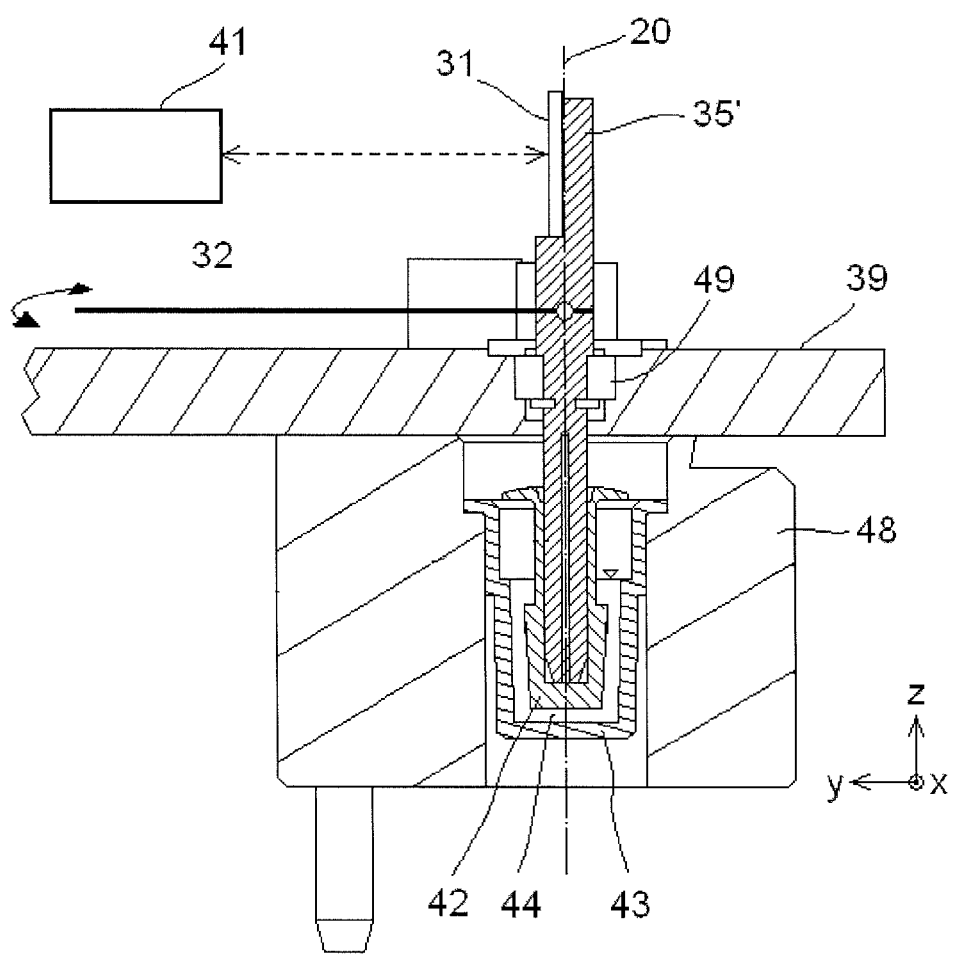
FIG. 1 is a schematic drawing of an example of thromboelastometry according to the state of the art.

The lower connector section 27 is also provided with a bore to be connected to a coupling shaft 35. To this end the coupling shaft 35 is formed with an interface section 36 which is preferably designed as a clip means. Other fixing means can be possible. The coupling shaft 35 further comprises a probe connector section 37 which is provided to be connected to a probe element 42 (see FIG. 1).

Furthermore the interface member 24 has a front 30 on which a detecting element 31, e.g. a mirror (see also FIG. 1 and FIG. 2), is fixed, e.g. by glue. The interface member 24 also comprises a receptacle 33 on the side of the front at the lower portion of the frame 26. A drive element 32, e.g. a spring wire, as already shown in FIG. 1 can be inserted into this receptacle 33.

In this example the upper bearing unit 14 and the lower bearing unit 21 are equipped with bearing cover plates 52. Said bearing cover plates 52 are disc-shaped and inserted into the through holes of the bearing units 14 and 21 in such a way that they surround portions of the shaft 10 which extends through passage holes of the bearing cover plates 52. These passage holes have an inner diameter which is a little bit greater than that of the outer diameter of the corresponding shaft portion. So the bearing cover plates 52 provide a certain sealing function. On the other hand the bearing cover plates 52 can centre the shaft 10. In use there is no friction between the bearing cover plates 52 and the corresponding shaft portions. In the example of FIG. 3 the bearing cover plate 52 of the upper bearing unit 14 is inserted into the lowest part of the bearing section 16 and co-operates with a cylindrical portion of the upper shaft toe 11 of the shaft 10. The bearing cover plate 52 of the lower bearing unit 21 is inserted into the upper part of the collar 22 and co-operates with a cylindrical portion of the shaft body 13 of the shaft 10.

An assembly of the measuring unit 1 can be done as following to achieve the assembled unit (see FIGS. 2 and 3).

First the lower bearing unit 21 is inserted into the lower bearing arm 4 and fixed as mentioned above. Then the interface member 24 is inserted into the recess 7 between upper bearing arm 3 and lower bearing arm 4 in such a way that the lower bearing 4 extends and protrudes through the opening 28 of the frame 26 of the interface member 24. The interface member 24 should be aligned with its bores to the rotation axis 20. Now the shaft 10 is inserted along the rotation axis 20 through the through hole in the upper bearing arm 3, through the bore of the upper connector section 25 of the interface member 24 into the lower bearing unit 21 so that the lower shaft toe 12 rests on the thrust plate 47 of the lower bearing unit.

Now the upper bearing unit 14 is inserted into the through hole of the upper bearing arm 3 and fixed as mentioned above, the movable bearing plate 46 resting on the upper shaft toe 11. Then the adjusting means 17 can be adjusted for a predefined pretension now or later.

The interface member 24 is shifted upwards on the shaft body 13 until the groove 51 can be fitted with a circlip 50. Then the interface member 24 is shifted downwards to rest on the circlip 50 to maintain a predefined axial position along the rotation axis 20. Now the interface member 24 can be fixed on the shaft body 13 by said fixing unit 29.

Thrust plate 47 and movable plate 46 comprise a dimple, respectively. The dimple will align the shaft 10 together with the interface member 24 and the coupling shaft 35.

Finally the coupling shaft 35, the detecting element 31 and the drive element 32 can be connected to the interface member 24.

When, in case of inserting the coupling shaft 35 and/or a probe element 42 (see FIG. 1) onto the coupling shaft 35, an axial force can be exerted via the interface member 24 on the shaft 10 and cause an axial movement of the shaft 10 in direction of the rotation axis 20 to the upper movable bearing 14. To limit said axial movement of the shaft 10 and the interface member 24 and a possible damage of the upper movable bearing 14 the measuring unit 1 can comprise axial stop means 60. Said stop means 60 can be formed in the shown embodiment e.g. by an upper shoulder of the interface member 24 or/and a shoulder of the shaft 10, said shoulder pointing to the upper bearing arm 3 and co-operating with a corresponding shoulder of the upper bearing arm 3 and/or the upper bearing unit 14.

Figure 4:
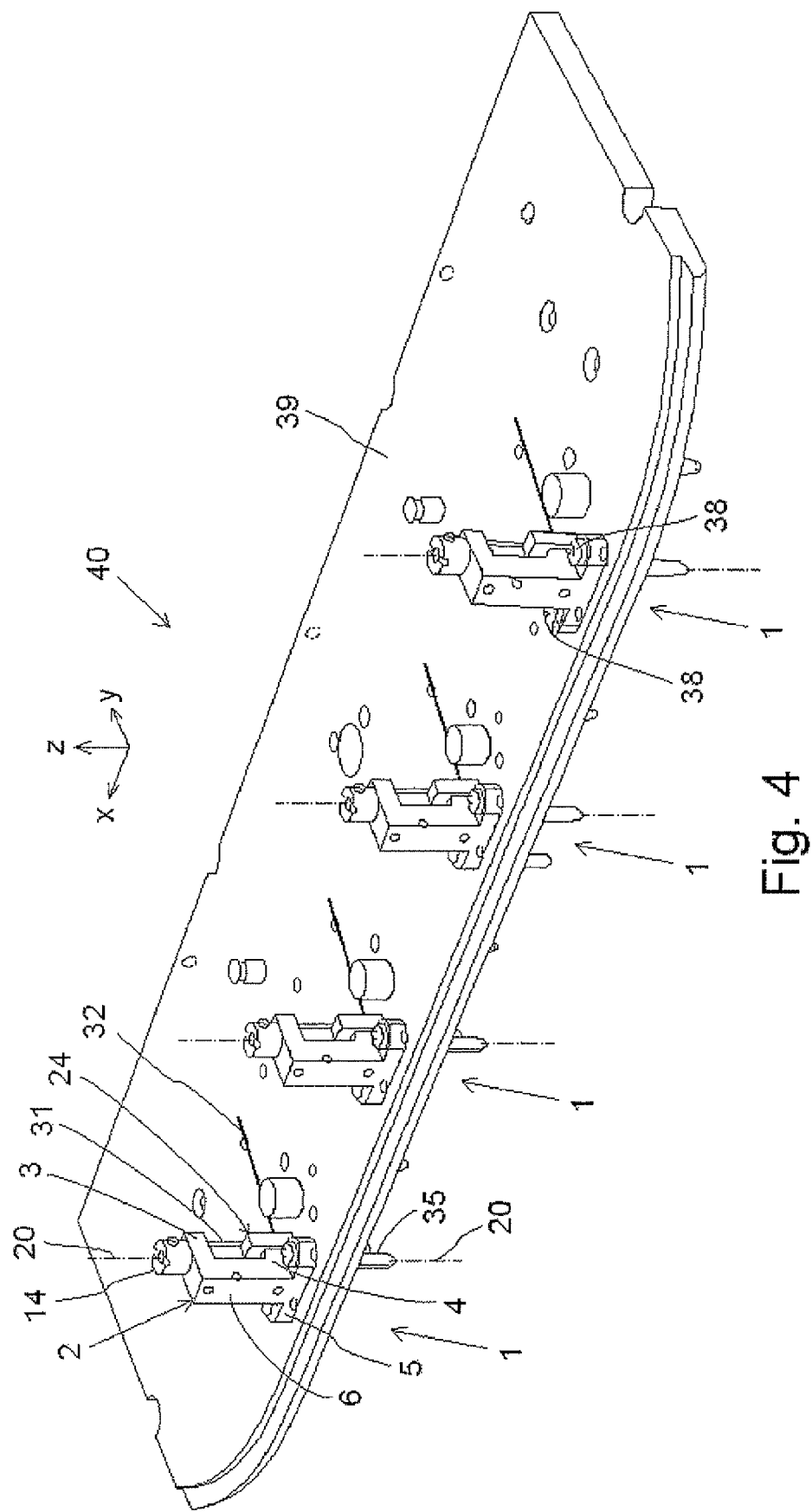
FIG. 4 is a perspective view of an exemplary embodiment of a measuring device according to the invention.

The assembled measuring unit 1 is shown in FIG. 3 and can be mounted on a base plate 39 of a measuring device 40 as shown in FIG. 4, which is a perspective view of an exemplary embodiment of a measuring device 40 according to the invention.

In the shown embodiment the measuring device 40 comprises four measuring units 1. The measuring units 1 are fixed on the base plate 39 by mounting elements, e.g. screws or clip fixing means, the coupling shafts 35 extending through corresponding openings in the base plate 39. The drive elements 32 extend in y-direction and can be driven by a not shown driving device to oscillate the respective interface members 24 with the thereto connected respective coupling shafts 35 (and corresponding parts as mentioned above) around the respective rotation axis 20.

Figure 5:
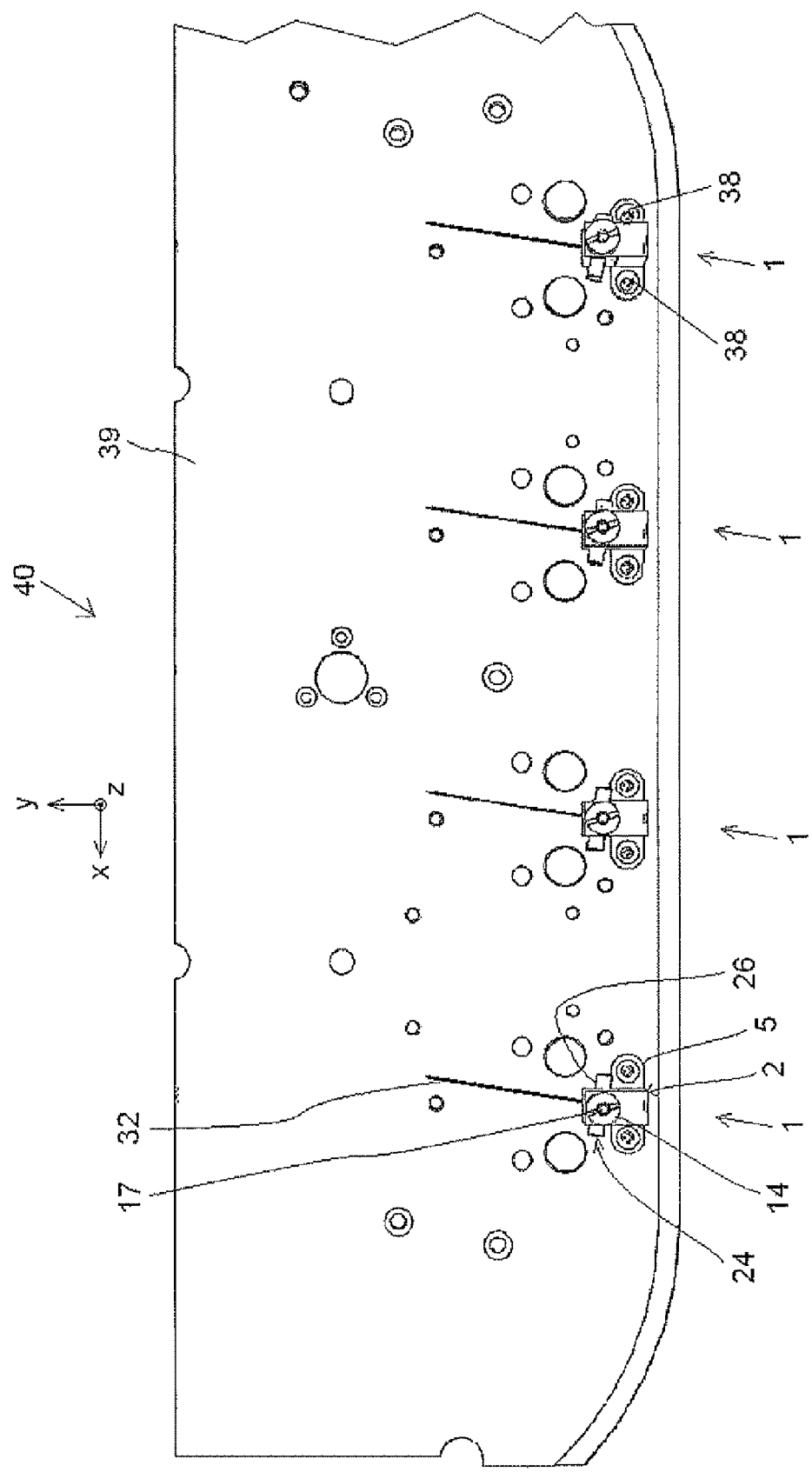
FIG. 5 is a top view of the measuring device of FIG. 4.

FIG. 5 is a top view of the measuring device 40 of FIG. 4. Here it is shown that the drive elements 32 and the connected interface members 24 are arranged in a specific angle to the y-direction.

Figure 6:
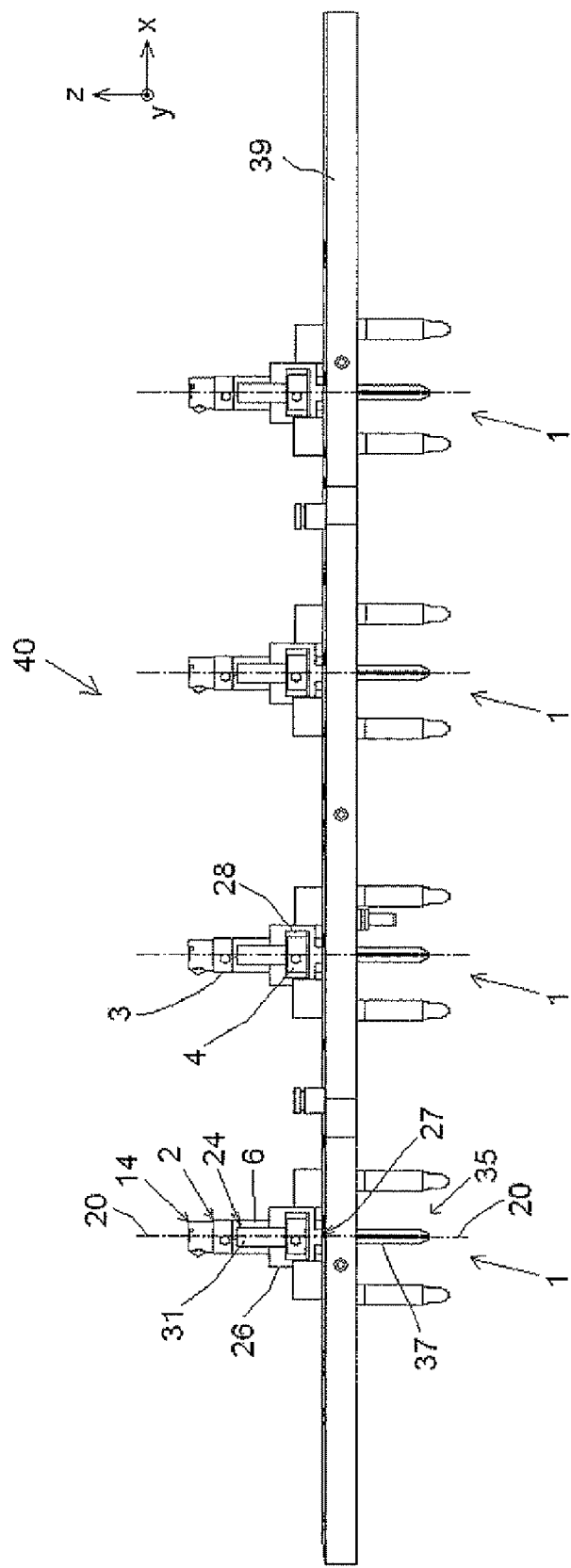
FIG. 6 is a view along y-direction of the measuring device of FIG. 4.

FIG. 6 is a view along y-direction of the measuring device of FIG. 4, wherein the detecting elements 31 can be seen from a front view.

Figure 7:
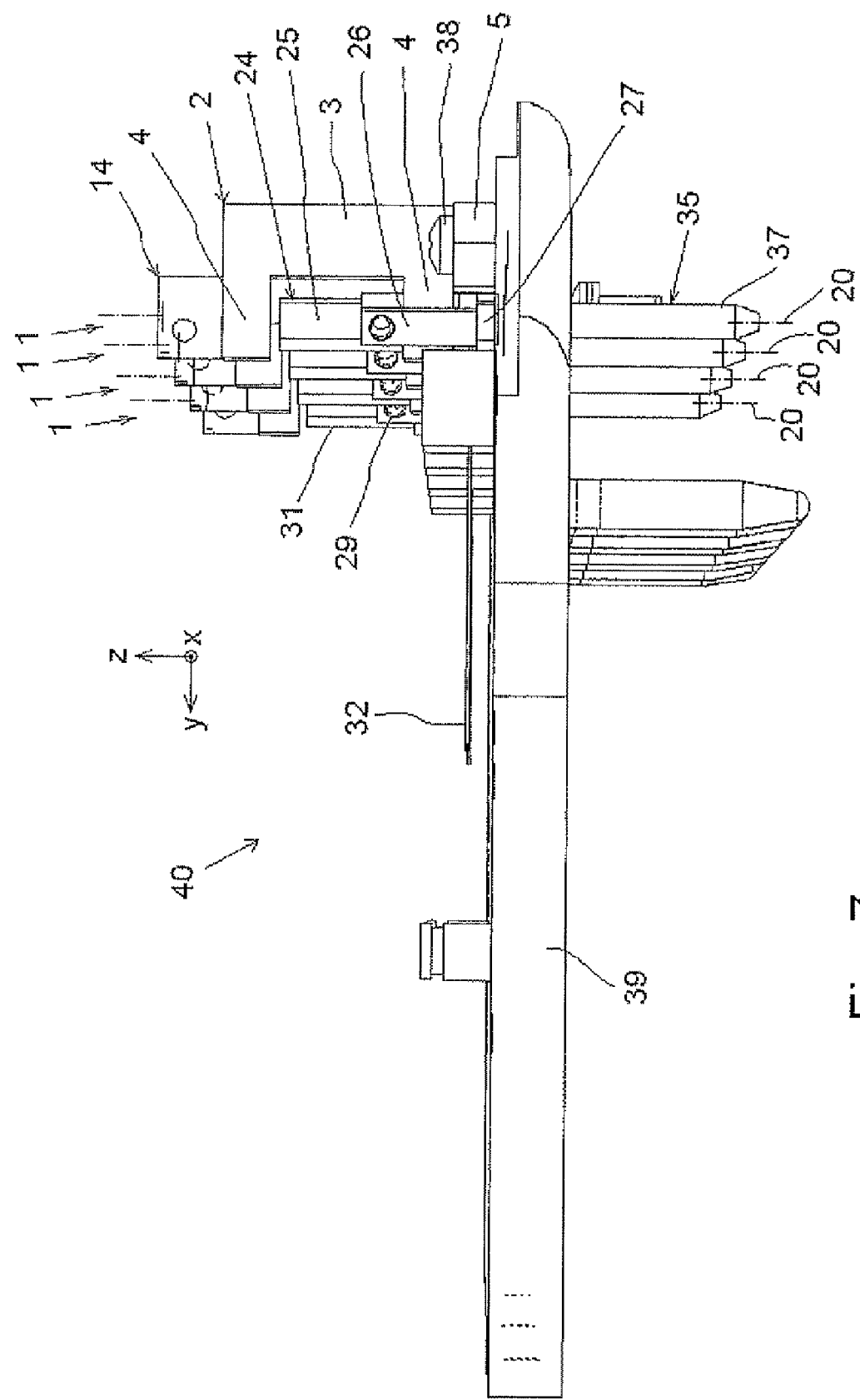
FIG. 7 is a perspective view in x-direction of the measuring device of FIG. 4.

Finally FIG. 7 is a perspective view in x-direction of the measuring device 40 of FIG. 4.

It will be apparent to those skilled in the art that changes and modifications can be made to the embodiments described above without departing from the spirit and scope of the present invention as defined by the appended claims.

LIST OF REFERENCE NUMERALS

1 Measuring unit
2 Support member
3 Upper bearing arm
4 Lower bearing arm
5 Base
6 Body
7 Recess
8 Upper fixing passage
9 Lower fixing passage
10 Shaft
11 Upper shaft toe
12 Lower shaft toe
13 Shaft body
14 Upper bearing unit
15 Fixing section
16 Bearing section
17 Adjusting means
18 Fixing means
19 Fixing passage
20 Rotation axis
21 Lower bearing unit
22 Collar
23 Bearing section
24 Interface member
25 Upper connector section
26 Frame
27 Lower connector section
28 Opening
29 Fixing unit
30 Front
31 Detecting element
32 Drive element
33 Receptacle
34 Fixing element
35, 35' Coupling shaft
36 Interface section
37 Probe connector section
38 Mounting element
39 Base plate
40 Measuring device
41 Detecting means
42 Probe element
43 Cup
44 Sample liquid
45 Spring
46 Movable bearing plate
47 Thrust bearing plate
48 Cup holder
49 Ball bearing
50 Groove
51 Circlip
52 Bearing cover plate

The invention claimed is:

1. A measuring unit for measuring viscoelastic characteristics of a blood sample, comprising:
a support member having at least one upper bearing arm with an upper bearing unit, at least one lower bearing arm with a lower bearing unit and a base for being attachable to a respective measuring system;
a shaft having shaft toes and being rotatably supported about a rotation axis by said upper bearing unit and said lower bearing unit, wherein said upper bearing unit, said lower bearing unit and said shaft toes form toe bearings, respectively; and
an interface member having a detecting element and a drive element, said interface member being fixed on said shaft and being connected to a coupling shaft with a probe connector section for measuring characteristics of said sample liquid;
wherein said interface member and the coupling shaft are coaxially aligned with said shaft, wherein said upper bearing unit is a moveable bearing being adjustable by adjusting means comprising a spring configured to adjust a pretension of the bearing units and the shaft.

2. The measuring unit according to claim 1, wherein said upper bearing unit and said lower bearing unit are removable inserts each being fixed in said respective bearing arm.

3. The measuring unit according to claim 1, wherein said lower bearing unit is a thrust bearing.

4. The measuring unit according to claim 1, wherein said upper bearing unit and said lower bearing unit comprise bearing plates made of a kind of jewel and/or ceramic.

5. The measuring unit according to claim 1, wherein said interface member comprises:
an upper connector section connected to said shaft;
a frame having an opening for a passage of said lower bearing arm of said support member;
a lower connector section connected to said coupling shaft;
a front for securing that said detecting element thereon; and
a receptacle for securing that said drive element therein.

6. The measuring unit according to claim 5, wherein said interface member further comprises a fixing unit for fixing said interface member to said shaft.

7. The measuring unit according to claim 6, wherein said fixing unit is at least one screw.

8. The measuring unit according to claim 6, wherein said fixing unit is formed having clip means cooperating with a corresponding clip means of said shaft.

9. The measuring unit according to claim 5, wherein said lower connector section is formed having clip means cooperating with corresponding clip means of an interface section of said coupling shaft.

10. The measuring unit according to claim 1, wherein said probe connector section of said coupling shaft is formed having clip means cooperating with corresponding clip means of a probe element being detachably fixed onto said probe connector section.

11. The measuring unit according to claim 1, wherein said detecting element is a mirror.

12. The measuring unit according to claim 1, wherein the drive element is a spring wire.

13. The measuring unit according to claim 1, comprising axial stop means to limit an axial movement of the shaft and the interface member.

14. The measuring unit according to claim 13, wherein the axial stop means are formed by a shoulder of the interface member and/or a shoulder of the shaft, said shoulder of the interface member and/or the shoulder of the shaft pointing to the upper bearing arm and co-operating with a corresponding shoulder of the upper bearing arm and/or corresponding shoulder of the upper bearing unit.

15. The measuring unit according to claim 1, wherein at least one of said upper bearing unit and said lower bearing unit comprises at least one bearing cover plate.

16. Measuring system for measuring characteristics of a sample liquid, in particular viscoelastic characteristics of a blood sample, comprising at least one measuring unit according to claim 1.

* * * * *